(12) United States Patent
Anderson

(10) Patent No.: US 11,766,237 B2
(45) Date of Patent: Sep. 26, 2023

(54) MULTI-MODE CAPACITIVE MICROMACHINED ULTRASOUND TRANSDUCER AND ASSOCIATED DEVICES, SYSTEMS, AND METHODS FOR MULTIPLE DIFFERENT INTRAVASCULAR SENSING CAPABILITIES

(71) Applicant: PHILIPS IMAGE GUIDED THERAPY CORPORATION, San Diego, CA (US)

(72) Inventor: David Anderson, Temecula, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 174 days.

(21) Appl. No.: 15/741,473

(22) PCT Filed: Jun. 20, 2016

(86) PCT No.: PCT/IB2016/053645
§ 371 (c)(1),
(2) Date: Jan. 2, 2018

(87) PCT Pub. No.: WO2017/001965
PCT Pub. Date: Jan. 5, 2017

(65) Prior Publication Data
US 2018/0360414 A1    Dec. 20, 2018

Related U.S. Application Data

(60) Provisional application No. 62/188,222, filed on Jul. 2, 2015.

(51) Int. Cl.
*A61B 8/00* (2006.01)
*A61B 8/04* (2006.01)
(Continued)

(52) U.S. Cl.
CPC .................. *A61B 8/12* (2013.01); *A61B 8/04* (2013.01); *A61B 8/445* (2013.01); *A61B 8/4483* (2013.01);
(Continued)

(58) Field of Classification Search
CPC ......... A61B 8/12; A61B 8/445; A61B 8/4483; A61B 8/04; A61B 8/4477; A61B 8/4416; A61B 8/06; B06B 1/0292
(Continued)

(56) References Cited

U.S. PATENT DOCUMENTS 6,443,901 B1   9/2002  Fraser
6,632,178 B1   10/2003 Fraser
(Continued)

*Primary Examiner* — Shahdeep Mohammed
*Assistant Examiner* — Amal Aly Farag

(57) ABSTRACT

Multi-mode capacitive micromachined ultrasound transducer (CMUT) and associated devices systems, and methods are provided. In an embodiment, an intravascular device includes a flexible elongate member having a proximal portion, a distal portion, and a first sensor assembly disposed at the distal portion of the flexible elongate member. The first sensor assembly comprising comprises a first array of capacitive micromachined ultrasonic transducers (CMUTs). The first sensor assembly comprises at least two of a pressure sensor, a flow sensor, or an imaging sensor. In some embodiments, the intravascular device further includes a second sensor assembly comprising a second array of CMUTs.

16 Claims, 6 Drawing Sheets

(51) Int. Cl.
    *A61B 8/12*    (2006.01)
    *B06B 1/02*    (2006.01)
    *A61B 8/06*    (2006.01)

(52) U.S. Cl.
    CPC .............. *B06B 1/0292* (2013.01); *A61B 8/06* (2013.01); *A61B 8/4416* (2013.01); *A61B 8/4477* (2013.01)

(58) Field of Classification Search
    USPC ........................................................ 600/438
    See application file for complete search history.

(56) References Cited

U.S. PATENT DOCUMENTS

| | | | |
|---|---|---|---|
| 6,659,954 B2 | 12/2003 | Robinson | |
| 8,203,912 B2 | 6/2012 | Roest | |
| 8,327,521 B2 | 12/2012 | Dirksen | |
| 2004/0236223 A1 | 11/2004 | Barnes | |
| 2005/0154299 A1* | 7/2005 | Hoctor | A61B 8/4236 600/437 |
| 2008/0269606 A1* | 10/2008 | Matsumura | A61B 8/12 382/128 |
| 2010/0246332 A1* | 9/2010 | Huang | A61B 8/12 367/181 |
| 2010/0262014 A1 | 10/2010 | Huang | |
| 2010/0268058 A1* | 10/2010 | Chen | A61B 8/4483 600/407 |
| 2011/0163630 A1 | 7/2011 | Klootwijk | |
| 2011/0190617 A1* | 8/2011 | Chen | A61B 5/0095 600/407 |
| 2011/0319766 A1 | 12/2011 | Tsuruno | |
| 2013/0331705 A1 | 12/2013 | Fraser | |
| 2014/0005521 A1 | 1/2014 | Koehler | |
| 2014/0139072 A1 | 5/2014 | Sudol | |
| 2014/0180087 A1* | 6/2014 | Millett | A61B 8/12 600/437 |
| 2014/0180140 A1 | 6/2014 | Alpert | |
| 2014/0187978 A1 | 7/2014 | Millett | |
| 2014/0236017 A1* | 8/2014 | Degertekin | A61B 8/12 600/462 |
| 2014/0275844 A1* | 9/2014 | Hoseit | A61B 8/4411 600/301 |
| 2014/0307528 A1 | 10/2014 | Dekker | |
| 2014/0332911 A1 | 11/2014 | Dirksen | |
| 2014/0375168 A1 | 12/2014 | Dirksen | |
| 2015/0016227 A1 | 1/2015 | Brock-Fisher | |
| 2015/0065922 A1 | 3/2015 | Kohler | |
| 2015/0086098 A1 | 3/2015 | Nair | |
| 2015/0272601 A1* | 10/2015 | Dixon | A61N 7/00 604/24 |

* cited by examiner

MULTI-MODE CAPACITIVE MICROMACHINED ULTRASOUND TRANSDUCER AND ASSOCIATED DEVICES, SYSTEMS, AND METHODS FOR MULTIPLE DIFFERENT INTRAVASCULAR SENSING CAPABILITIES

CROSS-REFERENCE TO RELATED APPLICATION

CROSS-REFERENCE TO RELATED APPLICATION

This application is the U.S. National Phase application under 35 U.S.C. §371 of International Application No. PCT/IB2016/053645, filed on Jun. 20, 2016, which claims the benefit of U.S. Provisional Patent Application No. 62/188,222, filed Jul. 2, 2015, which is hereby incorporated by reference in its entirety.

TECHNICAL FIELD

The present disclosure relates generally to intravascular sensing and, in particular, to sensing different modalities using capacitive micromachined ultrasound transducers (CMUTs). For example, some embodiments of the present disclosure provide an intravascular device with a CMUT sensor assembly operable to obtain pressure, flow, and/or imaging data within vasculature of a patient.

BACKGROUND

Innovations in diagnosing and verifying the level of success of treatment of disease have progressed from solely external imaging processes to include internal diagnostic processes. In addition to traditional external image techniques such as X-ray, MRI, CT scans, single-photon emission computed tomography (SPECT), fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter or a guide wire used for catheterization procedures. For example, known medical sensing techniques include intravascular ultrasound (IVUS), forward looking IVUS (FL-IVUS), fractional flow reserve (FFR) determination, Instant Wave-Free Ratio™ (iFR®) determination, a coronary flow reserve (CFR) determination, optical coherence tomography (OCT), trans-esophageal echocardiography, and image-guided therapy.

Commercial sensors usually implement lead-zirconate-titanate (PZT) or piezoelectric micro-machined ultrasound transducers (PMUTs) to acquire imaging, flow, pressure, and other types of intravascular data. While PZT and PMUT sensors have been satisfactory in most respects, CMUT sensors are being considered more recently as an alternative technology. CMUT sensors operate on the principle of detecting capacitance changes when a membrane is deflected. Extant intravascular devices with CMUT sensors, however, are usually limited to one sensing modality, such as ultrasound imaging.

Thus, there remains a need for intravascular sensing system that provides multi-mode sensing capabilities.

SUMMARY

Embodiments of the present disclosure provide an improved intravascular device for sensing multiple types of intravascular data with capacitive micromachined ultrasound transducers (CMUTs). In some circumstances, the CMUTs can be divided or organized into zones. Each zone can obtain data corresponding to a different intravascular data type (e.g., pressure, flow, imaging, etc.). In other circumstances, the CMUTs can be cycle through different operations (e.g., pressure, flow, and imaging, etc.) so that the same CMUTs obtain data corresponding to the different intravascular data types at various times.

In an exemplary aspect, the present disclosure is directed to an intravascular device. The intravascular device includes a flexible elongate member having a proximal portion and a distal portion; and a first sensor assembly disposed at the distal portion of the flexible elongate member, the first sensor assembly comprising a first array of capacitive micromachined ultrasonic transducers (CMUTs); wherein the first sensor assembly comprises at least two of a pressure sensor, a flow sensor, or an imaging sensor.

In some embodiments, the first sensor assembly is disposed in an annular configuration about the flexible elongate member. In some embodiments, the first sensor assembly is disposed at a distal end of the flexible elongate member. In some embodiments, the first sensor assembly is disposed in at least one of a side-looking or forward-looking orientation. In some embodiments, the intravascular device further includes a second sensor assembly comprising a second array of CMUTs. In some embodiments, the first sensor assembly is disposed in one of a side-looking or forward-looking orientation, and wherein the second sensor assembly is disposed in the other of a side-looking or forward-looking orientation. In some embodiments, the flexible elongate member comprises a guide wire or a catheter. In some embodiments, the first array of CMUTs is arranged in a planar or non-planar configuration. In some embodiments, different portions of the first array of CMUTs comprise the pressure sensor, the flow sensor, or the imaging sensor. In some embodiments, the first sensor assembly comprises the pressure sensor, the flow sensor, or the imaging sensor at different times.

In an exemplary aspect, the present disclosure is directed to an intravascular system. The system includes an intravascular device configured to be inserted into vasculature of a patient, the intravascular device comprising: a flexible elongate member having a proximal portion and a distal portion, a sensor assembly disposed at the distal portion of the flexible elongate member, the sensor assembly comprising an array of capacitive micromachined ultrasonic transducers (CMUTs); wherein the sensor assembly comprises at least two of a pressure sensor, a flow sensor, or an imaging sensor; and a computing device in communication with the intravascular device and configured to receive intravascular data obtained by the sensor assembly.

In some embodiments, the intravascular system further includes a patient interface module (PIM) in communication with the intravascular device and the computing device. In some embodiments, the intravascular system further includes a display in communication with the computing device and configured to display graphical representations of the intravascular data. In some embodiments, different portions of the array of CMUTs comprise the pressure sensor, the flow sensor, or the imaging sensor. In some embodiments, the computing device is configured to receive pressure data, flow data, or imaging data obtained by the respective different portions of the array of CMUTs. In some embodiments, the computing device is configured to control the respective different portions of the array of CMUTs to obtain pressure data, flow data, or imaging data. In some embodiments, the sensor assembly comprises the pressure sensor, the flow sensor, or the imaging sensor at different times. In some embodiments, the computing device is configured to receive pressure data, flow data, or imaging data obtained by the sensor assembly at the respective different times. In some embodiments, the computing device configured to control the sensor assembly to obtain pressure data, flow data, or imaging data at the respective different times.

In an exemplary aspect, the present disclosure is directed to a method of obtaining intravascular data. The method includes receiving, at a computing device, first and second intravascular data associated with different modalities and obtained by an intravascular device inserted into the vasculature of a patient and in communication with the computing device, the intravascular device comprising: a flexible elongate member having a proximal portion and a distal portion, a sensor assembly disposed at the distal portion of the flexible elongate member, the sensor assembly comprising an array of capacitive micromachined ultrasonic transducers (CMUTs); wherein the sensor assembly comprises at least two of a pressure sensor, a flow sensor, or an imaging sensor; processing, at the computing device, the first and second intravascular data; and providing, from the computing device to a display in communication with the computing device, graphical representations of the processed first and second types of intravascular data for display.

In some embodiments, the first and second intravascular data are simultaneously obtained by the intravascular device. In some embodiments, different portions of the array of CMUTs comprise the pressure sensor, the flow sensor, or the imaging sensor. In some embodiments, the method further includes controlling the respective different portions of the array of CMUTs to obtain pressure data, flow data, or imaging data. In some embodiments, the first and second intravascular data are obtained by the intravascular device at different times. In some embodiments, the sensor assembly comprises the pressure sensor, the flow sensor, or the imaging sensor at different times. In some embodiments, the method further includes controlling the sensor assembly to obtain pressure data, flow data, or imaging data at the respective different times.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
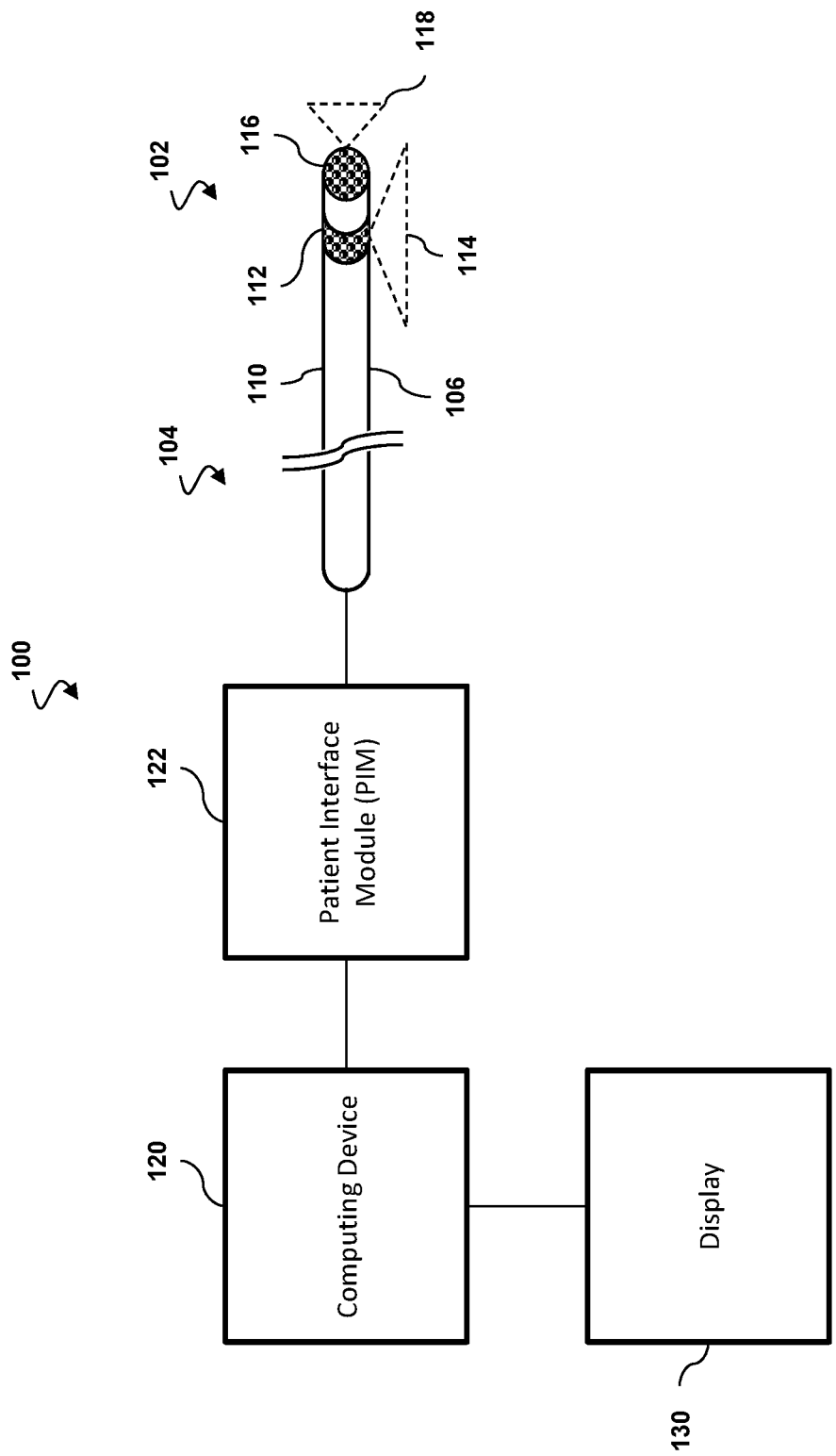
FIG. 1 is a diagrammatic schematic view of an intravascular sensing system according to aspects of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one or more implementations may be combined with the features, components, and/or steps described with respect to other implementations of the present disclosure. For simplicity, in some instances the same reference numbers are used throughout the drawings to refer to the same or like parts.

The present disclosure relates generally to intravascular sensing devices, systems and methods having a CMUT array operable to obtain data associated with multiple, different intravascular modalities. In some embodiments, the different portions of the CMUT array are operable as different ones of a pressure sensor, a flow sensor, an imaging sensor, etc. In some embodiments, the CMUT array is operable as the pressure sensor, the flow sensor, the imaging sensor, etc., at different times. Multiple CMUT arrays may be provided on the intravascular device. The positioning and orientation each CMUT array can be selected to optimize collection of data associated with a particular intravascular modality.

The intravascular sensing devices, systems and methods of the present disclosure provide multiple advantages. For example, utilizing a CMUT array may result in fewer conductors extending along the length of the intravascular device. For example, a CMUT includes two conductors extending respectively to two electrodes. The capacitance changes between the electrodes can be representative of the obtained intravascular data. A CMUT array also advantageously utilizes multiple individual CMUTs that are in communication. In that regard, individual CMUTs and/or zones within CMUT array can be individually addressed and/or otherwise controlled. A CMUT array may also advantageously reduce processing carried out by a processor and/or data stored on a memory because detecting capacitance changes are less process/memory intensive. The CMUT array also allows for smaller, minimally invasive sensors and intravascular devices.

Referring to FIG. 1, shown therein is an intravascular sensing system 100. The system 100 includes an intravascular device 110 having a sensor assemblies 112 and 116, a computing device 120, a patient interface module (PIM) 122, and a display 130. The intravascular sensing system 100 can be implemented, for example, in a catheterization lab of a hospital or other medical services provider. The intravascular device 110 is also illustrated in more detail in FIG. 2.

Figure 2:
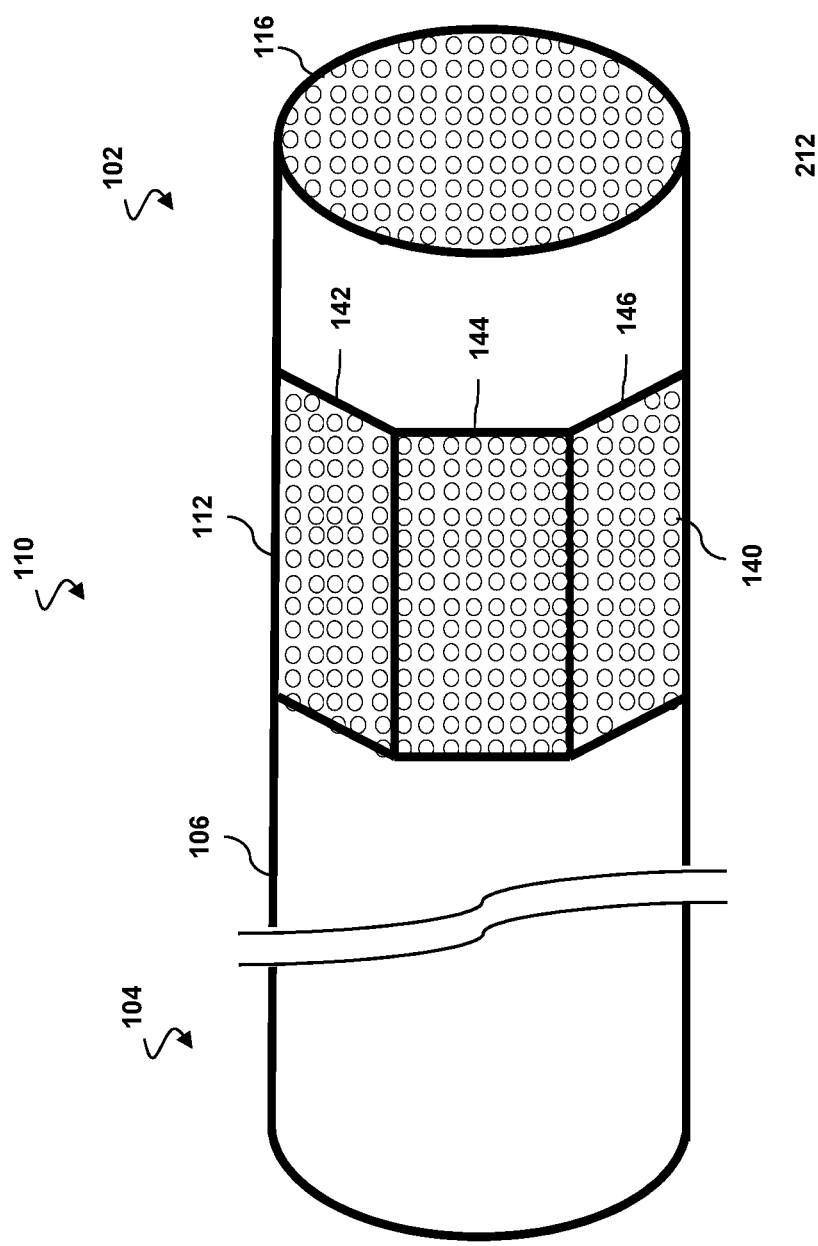
FIG. 2 is a diagrammatic side view of an intravascular device according to aspects of the present disclosure.

Referring to both FIGS. 1 and 2, the intravascular device 110 includes flexible elongate member 106 and sensor assemblies 112, 116. The intravascular device 110 is configured to be inserted into a patient's vasculature by a user, such as a surgeon or other medical profession, during an intravascular sensing procedure. In that regard, the intravascular device 110 can be a catheter, guide wire, or guide catheter. The flexible elongate member 106 has a distal portion 102 and a proximal portion 104. The dimensions of the flexible elongate member 106, including the length and diameter, can vary in different embodiments. For example, the flexible elongate member 106 can be sized and shaped for use in the coronary arteries, peripheral vessels, heart, and/or other areas of the patient's vasculature.

In different embodiments, the intravascular device 110 can include one, two, three, four, or more sensor assemblies coupled to the flexible elongate member 106. FIGS. 1 and 2 illustrate two sensor assemblies 112, 116 disposed at the distal portion 102 of the intravascular device 110. Each sensor assembly 112, 116 includes an array or plurality of CMUTs. In that regard, each array can be arranged in a planar, non-planar, and/or other suitable configuration. For example, an array can include CMUTs laid out substantially in two dimensions (as shown, e.g., in FIG. 4). An array can also be arranged in a non-planar configuration. For example, an array with CMUTs laid out substantially in two dimensions can be arranged in a cylindrical or non-planar configuration when wrapped around an intravascular device (e.g., sensor assembly 112 of FIGS. 1 and 2). It is understood that a CMUT array can be described as two-dimensional or three-dimensional. In that regard, an array with CMUTs laid out substantially in two dimensions (x and y) extends at least some value in the third dimension (z). Other suitable two-dimensional or three-dimensional configurations are also contemplated.

An outermost of layer of each CMUT is visible in FIGS. 1 and 2. For example, each CMUT includes a sensor membrane or diaphragm 140 that is configured to be deflected upon application of voltage to create a pressure wave (e.g., to transmit an ultrasound signal) or detect/measure pressure that is electronically sensed as a change in capacitance (e.g., upon receipt of an ultrasound echo). The CMUTs can be similar to those described in U.S. Pat. No. 8,203,912, titled "CMUTs with a high-k dielectric," and issued Jun. 19, 2012; U.S. Pat. No. 6,632,178, titled "Fabrication of capacitive micromachined ultrasonic transducers by micro-stereolithography," and issued Oct. 14, 2003; U.S. Pat. No. 8,327,521, titled "Method for production and using a capacitive micro-machined ultrasonic transducer," and issued Dec. 11, 2012; U.S. Pat. No. 6,443,901, titled "Capacitive micromachined ultrasonic transducers," and issued Jun. 15, 2000; U.S. Pat. No. 6,659,954, titled "Micromachined ultrasound transducer and method for fabricating same," and issued Dec. 9, 2003; U.S. application Ser. No. 14/382,560, titled "Capacitive micro-machined ultrasound transducer device with charging voltage source," and filed Sep. 3, 2014; U.S. application Ser. No. 14/125,958, titled "Ultrasound transducer assembly and method of manufacturing the same," and filed Dec. 13, 2013; U.S. application Ser. No. 14/365,647, titled "Ultrasound transducer device and method of manufacturing the same," and filed Jun. 16, 2014; U.S. application Ser. No. 14/370,110, titled "Capacitive micro-machined transducer and method of manufacturing the same," and filed Jul. 1, 2014; U.S. application Ser. No. 14/369,341, titled "Capacitive micro-machined transducer and method of manufacturing the same," and filed Jun. 27, 2014; U.S. application Ser. No. 13/062,744, titled "Capacitive micromachine ultrasound transducer," and filed Mar. 8, 2011; U.S. application Ser. No. 13/885,791, titled "Catheter comprising capacitive micromachined ultrasonic transducers with an adjustable focus," and filed Sep. 3, 2013; U.S. application Ser. No. 14/000,891, titled "Ultrasonic CMUT with suppressed acoustic coupling to the substrate," and filed Mar. 13, 2012; and U.S. application Ser. No. 14/365,647, titled "Ultrasound transducer device and method of manufacturing the same," and filed Jun. 16, 2014, the entireties of which are incorporated by reference herein.

The sensor assemblies 112, 116 can be positioned, arranged, oriented, and/or otherwise disposed on the flexible elongate member 106 in any desired manner. For example, the sensor assemblies 112, 116 can be positioned at any point along the length of the flexible elongate member 106. The sensor assemblies 112, 116 can include a linear, rectangular, circular, elliptical, annular, and/otherwise suitably shaped array of CMUTs. The sensor assemblies 112, 116 may be coupled to the flexible elongate member 106 in a side-looking, forward-looking, other suitable orientation, and/or combinations thereof. In the illustrated embodiment, the sensor assembly 112 is disposed in an annular configuration around or about the flexible elongate member 106. The sensor assembly 112 can be disposed in a side-looking orientation that covers the field of view 114, for example. In that regard, the sensor assembly 112 may be advantageously positioned for obtaining intravascular imaging and/or pressure data. The sensor assembly 116 is disposed at the distal end of the flexible elongate member 106. The sensor assembly 116 is disposed in a forward-looking orientation that covers the field of view 118, for example. In that regard, the sensor assembly 116 may be advantageously positioned for obtaining intravascular imaging, pressure data, and/or flow data. In some instances, two or more sensor assemblies can be coupled to the flexible elongate member 106 with known separation distance(s) (e.g., 10 cm, 20 cm, etc.). For example, in an embodiment with three sensor assemblies, the first and second sensor assemblies can be separated by a first distance, and the first and third sensor assemblies can be separated by a second distance. In such an embodiment, the sensor assemblies may be advantageously utilized for sensing pressure to compute one or more pressure quantities (iFR, FFR, Pd/Pa, etc.). For example, a first sensor assembly can be positioned at a location proximal to a lesion (e.g. at or near the aorta, with a coronary artery, etc.), and the second and third sensor assemblies can be positioned at locations distal to the lesion. The sensor assemblies can thus measure a proximal pressure (e.g., Pa) and two distal pressures (e.g., $Pd_1$, $Pd_2$, at different distances from the proximal pressure measurement location), for example, while the intravascular device is held stationary within the vasculature.

Sensor assemblies 112, 116 can be substantially unitary components or formed of constituent elements. For example, the sensor assembly 116 can be a single component. For example, the sensor assembly 112 can include a plurality of panels 142, 144, 146. The sensor assembly 112 can include other panels on the side of the intravascular device 110 that is not visible in FIGS. 1 and 2. The panels 142, 144, 146 are shown to be generally rectangular, though they may be otherwise shaped in different embodiments. The sensor assembly 112 can be manufactured with the panels 142, 144, 146 in the planar configuration. During assembly of the intravascular device 110, the panels 142, 144, 146 can be folded into an annular configuration. In that regard, the sensor assembly 116 may be operated in a similar manner as a solid-state or phased array piezoelectric transducer array if so desired by the user. For example, individual panels may be activated one at a time in a sweeping manner (e.g., to transmit ultrasound signal, to receive ultrasound signal, etc.).

The sensor assemblies 112, 116 are configured to sense, collect, and/or otherwise obtain imaging data, pressure data, Doppler or velocity flow data, volume or mass flow data, temperature data, other diagnostic data, and/or combinations thereof. In some embodiments, the sensor assembly 112 and the sensor assembly 116 are operable to obtain different types or modalities of intravascular data. For example, the sensor assembly 112 obtains pressure data while the sensor assembly 116 obtains flow data. In some embodiments, the sensor assembly 112 and/or the sensor assembly 116 may each be fixedly configured to obtain one type of intravascular data. In that regard, the sensor assembly 112 and/or the sensor assembly 116 can be optimized, e.g., during manufacture, to obtain data associated with a particular intravascular modality. In some embodiments, the sensor assemblies 112, 116 are operable to obtain data associated with the same intravascular modality.

In some embodiments, the sensor assembly 112 and/or the sensor assembly may be variably configured to obtain data associated with different intravascular modalities. In that regard, the sensor assemblies 112, 116 are operable to obtain any one or more intravascular sensing modalities. For example, the sensor assembly 112 can obtain pressure data and later obtain flow data. Such an embodiment is described in greater detail with respect to FIG. 5. In other embodiments, the data type obtained by the sensor assemblies 112, 116 can be selected and controlled by a user (e.g., before and/or during the intravascular sensing procedure). In some embodiments, one of the sensor assembly 112 and/or the sensor assembly 116 is fixedly configured to obtain one type of intravascular data while the other of the sensor assembly 112 and/or the sensor assembly 116 is variably configured to obtain different types of intravascular data.

In some embodiments, different portions of the array of CMUTs forming the sensor assembly (e.g., sensor assembly 112, the sensor assembly 116, etc.) are operable to obtain intravascular data associated with different modalities. As described in greater detail with respect to FIGS. 3 and 4, a portion of the CMUT array can be configured to obtain imaging data, a portion can be configured to obtain pressure data, a portion may be configured to obtain flow data, etc. In some embodiments, the different portions of the sensor assembly can each be fixedly configured to obtain one type of intravascular data. In that regard, the different portions may be optimized, e.g., during manufacture, to obtain the respective data type. In some embodiments, the different portions of the CMUT array can each variably configured to obtain different types of intravascular data. For example, a first portion of the CMUT array can obtain pressure data and later obtain flow data. In other embodiments, the data type obtained by different portions of the CMUT array can be selected and controlled by a user (e.g., before and/or during the intravascular sensing procedure).

The intravascular device 110 can include various other components to facilitate transmission of signals between the sensor assemblies 112, 116, the computing device 120, and/or the PIM 122. For example, the intravascular device 110 can include conductors that electrically couple the sensor assemblies 112, 116, the computing device 120, and/or the PIM 122. In that regard, the conductors may be in contact with electrodes of the CMUT, a particular portion of the CMUT array, and/or the sensor assemblies 112, 116. The intravascular device 110 can also include integrated circuit controller chips(s) or application-specific integrated circuit(s) configured to control the sensor assemblies 112, 116 and/or particular portions thereof. For example the controller chip(s) may activate transmitter circuitry to generate an electrical pulse to excite the CMUT array element(s) and to accept amplified echo signals received from the CMUT array element(s) via amplifiers included on the controller chip(s). The controller chip(s) can also provide to signals to the sensor assemblies 112, 116 and/or portions thereof to obtain data associated with particular intravascular sensing modalities. In that regard, controller chip(s) may be configured to perform pre-processing on the obtained data to determine the modality associated therewith. In some instances, controller chip(s) can perform digital signal processing functions, amplifier functions, wireless functions, as described, e.g., in U.S. application Ser. No. 14/133,331, titled "Intravascular Devices Having Information Stored Thereon And/Or Wireless Communication Functionality, Including Associated Devices, Systems, And Methods," and filed Dec. 18, 2013, which is incorporated by reference herein in its entirety.

Referring again to FIG. 1, the intravascular device 110 and/or the sensor assemblies 112, 116 are in communication the computing device 120 and/or the PIM 122. For example, the computing device 120 receives the intravascular data obtained by the intravascular device 110 and processes the intravascular data to generate a graphical representation of the obtained data. For example, the computing device 120 can receive pressure data from the sensor assembly 112 and/or the sensor assembly 116 by way of the PIM 122. The computing device 120 can process the data to compute one or more pressure quantities (e.g., FFR, iFR, etc.). In some embodiments, the computing device 120 can co-register the obtained data with a fluoroscopic/angiographic image of the vessel. The computing device 120 can output a graphical representation of the processed data, such as the pressure quantities overlaid on the image of the vessel to the display 130. As another example, the computing device 120 can receive imaging data representative of ultrasound echoes from the sensor assembly 112 and/or the sensor assembly 116. The computing device 120 can process the data to reconstruct an image of the tissue structures in the medium surrounding the sensor assembly 112 and/or the sensor assembly 116. The image provided to and displayed on the display 130 can be similar to a B-scan image representative of the two-dimensional anatomical structure of the tissue in a plane perpendicular to the longitudinal axis of intravascular device 110, with brightness at any point of the image representing of the strength of the echo signal received from the corresponding location within the tissue. In some embodiments, the imaging data obtained by the intravascular device 110 is used for lumen mapping. The computing device 120 can receive and process the imaging data to generate an image illustrating the contours of a lumen of the patient's vasculature. As yet another example, the computing device 120 can receive and process flow data to generate a visual representation of movement of elements in the medium surrounding the sensor assembly 112 and/or the sensor assembly 116, such as blood flow. In some embodiments, the computing device 120 may carry out one or more functions described above with respect to the controller chip(s). For example, the computing device 120 can generate and provide signals to the sensor assemblies 112, 116 and/or portions thereof to obtain data associated with particular intravascular sensing modalities.

The computing device 120 can be generally representative of any device suitable for performing the processing and analysis techniques discussed within the present disclosure. In some embodiments, the computing device 120 includes a processor, random access memory, and a storage medium. The computing device 120 is operable to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 120 is a console device. In some particular instances, the computing device 120 is similar to the s5™ Imaging System or the s5i™ Imaging System, each available from Volcano Corporation.

In some instances, the computing device 120 is portable (e.g., handheld, on a rolling cart, etc.). Further, it is understood that in some instances the computing device 120 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

The PIM 122 that facilitates communication of signals between the computing device 120 and the sensor assemblies 112, 116 of the intravascular device 110. In some embodiments, the PIM 122 performs preliminary processing of the obtained intravascular data prior to relaying the data to the computing device 120. In examples of such embodiments, the PIM 122 performs amplification, filtering, and/or aggregating of the data. In an embodiment, the PIM 122 also supplies high- and low-voltage DC power to support operation of the intravascular device 110 including circuitry within the sensor assemblies 112, 116. The PIM 122 transfers the received intravascular data to the computing device 120 where, among other things, a graphical presentation of the processed data is generated displayed on the display 130. In some embodiments, the PIM 122 is configured to perform wireless functions related to, e.g., the transmission and receipt of intravascular data. An exemplary PIM is described, for example, in U.S. application Ser. No. 14/133,406, titled "Wireless Interface Devices, Systems, and Methods for Use with Intravascular Pressure Monitoring Devices," and filed Dec. 18, 2013, the entirety of which is incorporated by reference herein.

Figure 3:
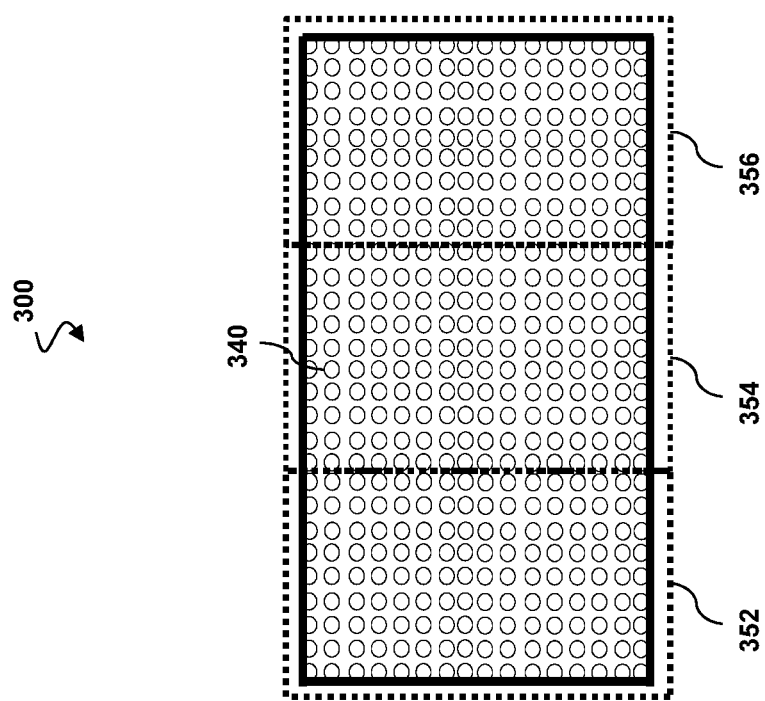
FIG. 3 is a diagrammatic top view of an array of CMUTs according to aspects of the present disclosure.

Referring to FIG. 3, shown therein is a top view of a CMUT array 300. In that regard, the array 300 can comprise an entire or partial sensor assembly. For example, the CMUT array 300 may be the sensor assembly 112 or an individual panel 142, 144, 146 (FIG. 2). The CMUT array 300 includes a plurality of sensor membranes 340. In that regard, the size of the sensor membranes 340 is not necessarily to scale in the drawings. In some embodiments, the diameter of each of the sensor membranes 340 can be between approximately 1 µm and approximately 200 µm, between approximately 10 µm and approximately 200 µm, between approximately 20 µm and approximately 200 µm, and/or other suitable values both larger and smaller.

In some embodiments, different portions or zones of the CMUT array 300 are operable to obtain data associated with different intravascular modalities. For example, zone 352 can be configured to obtain pressure data, zone 354 can be configured to obtain flow data, and zone 356 can be configured to obtain imaging data. That is, different portions of the CMUT array 300 comprise the pressure sensor, the flow sensor, and/or the imaging sensor. While the zones 352, 354, 356 are shown to be similarly sized and shaped, it is understood that the zones may be sized and shaped differently from one another. Similarly, the illustrated embodiment illustrates rectangular zones. In various embodiments, other shapes, such as circles, ellipses, polygons, etc. are used to define the zones. In some embodiments, individual CMUTs and/or zones that perform the same function are arranged continuously or continuously in an array. In other embodiments, individual CMUTs and/or zones that are spaced from one another (e.g., discontinuous or discontinuous) in an array perform the same function. For example, a computing device can process the intravascular data collected at different zones to generate a composite. In some instances, the individual zones can be described as individual pressure sensors, flow sensors, and/or imaging sensors.

Figure 4:
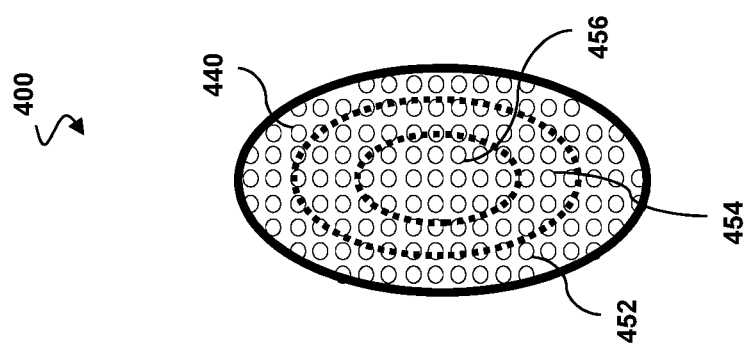
FIG. 4 is a diagrammatic top view of an array of CMUTs according to aspects of the present disclosure.

Referring to FIG. 4, shown therein is a top view of a CMUT array 400. CMUT array 400 is similarly in manner respects to the CMUT array 300 (FIG. 3). In that regard, the array 400 can comprise an entire or partial sensor assembly. For example, the CMUT array 300 may be the sensor assembly 116 (FIG. 2). The CMUT array 400 includes a plurality of sensor membranes 440. In some embodiments, different portions or zones of the CMUT array 400 are operable to obtain data associated different intravascular modalities. For example, zone 452 can be configured to obtain pressure data, zone 454 can be configured to obtain flow data, and zone 456 can be configured to obtain imaging data. That is, different portions of the CMUT array 400 comprise the pressure sensor, the flow sensor, or the imaging sensor. In the illustrated embodiment, the zone 456 is circular while the zones 452 and 454 are annular, ring, or donut shaped. The zones 452, 454, 456 are also concentric. It is understood that the zones may be sized and shaped differently in various embodiments.

Figure 5:
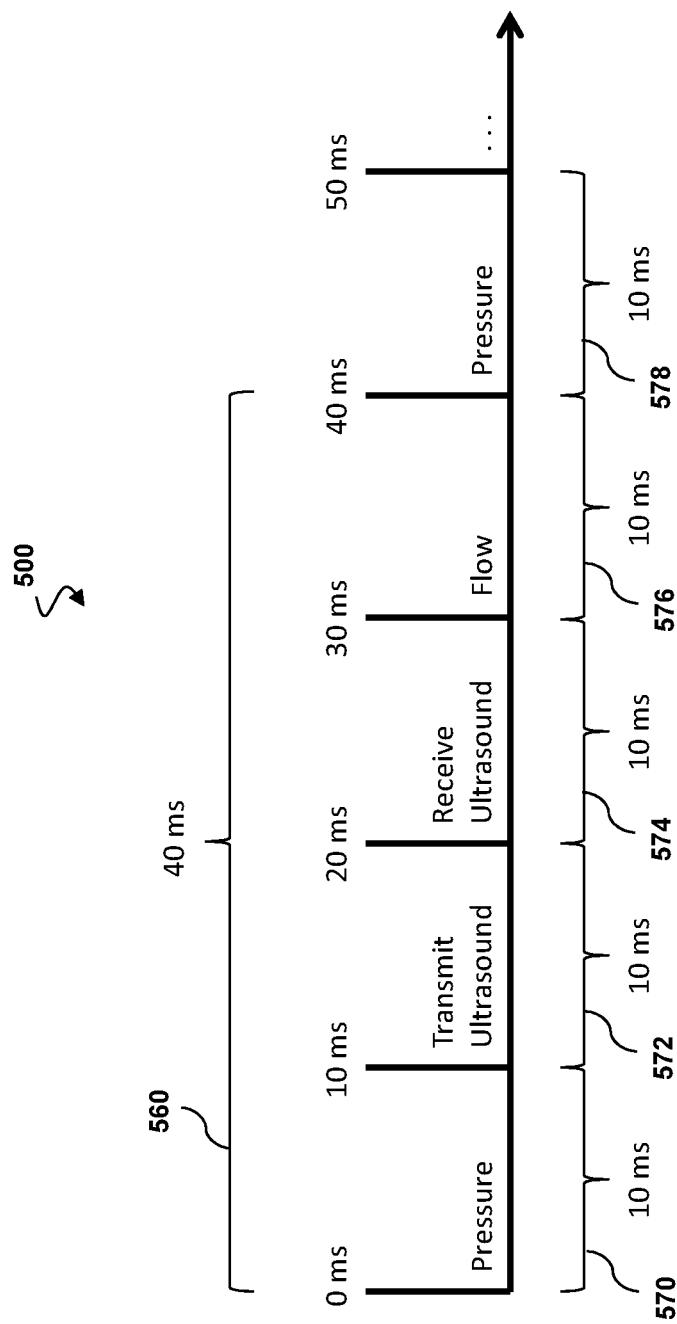
FIG. 5 is a diagrammatic illustration of an intravascular data acquisition protocol according to aspects of the present disclosure.

Referring to FIG. 5, shown therein is an illustration representative of an intravascular data collection protocol 500. Generally, the protocol 500 is representative of one sensor assembly comprising the pressure sensor, the flow sensor, and/or the imaging sensor at different times. By rapidly cycling through different functions of the sensor assembly, the same sensor assembly can be utilized to obtain data associated with multiple intravascular modalities. For example, the protocol 500 may be implemented using the sensor assembly 112 and/or the sensor assembly 116 (FIGS. 1 and 2).

The protocol 500 includes intervals 570, 572, 574, 576, 578 during which the sensor assembly performs different functions. The intervals 570, 572, 574, 576, 578 are shown to each be 10 ms in the illustrated embodiment. It is understood that the duration of the intervals 570, 572, 574, 576, 578 may be different in other embodiments. Similarly, it is understand that one or more intervals 570, 572, 574, 576, 578 can have a duration that is longer or shorter than one or more other intervals 570, 572, 574, 576, 578. For example, during the interval 570, the sensor assembly is operable to obtain pressure data. The intervals 572, 574 can be associated with imaging data. In particular, during the interval 572, the sensor assembly is operable to transmit ultrasound waves, and during the interval 574, the sensor assembly is operable to receive ultrasound echoes reflected from tissues structures within the patient's vascular. During the interval 576, the sensor assembly is operable to obtain flow data. The cycle 560 can repeat multiple times for the total duration of the sensing procedure.

Figure 6:
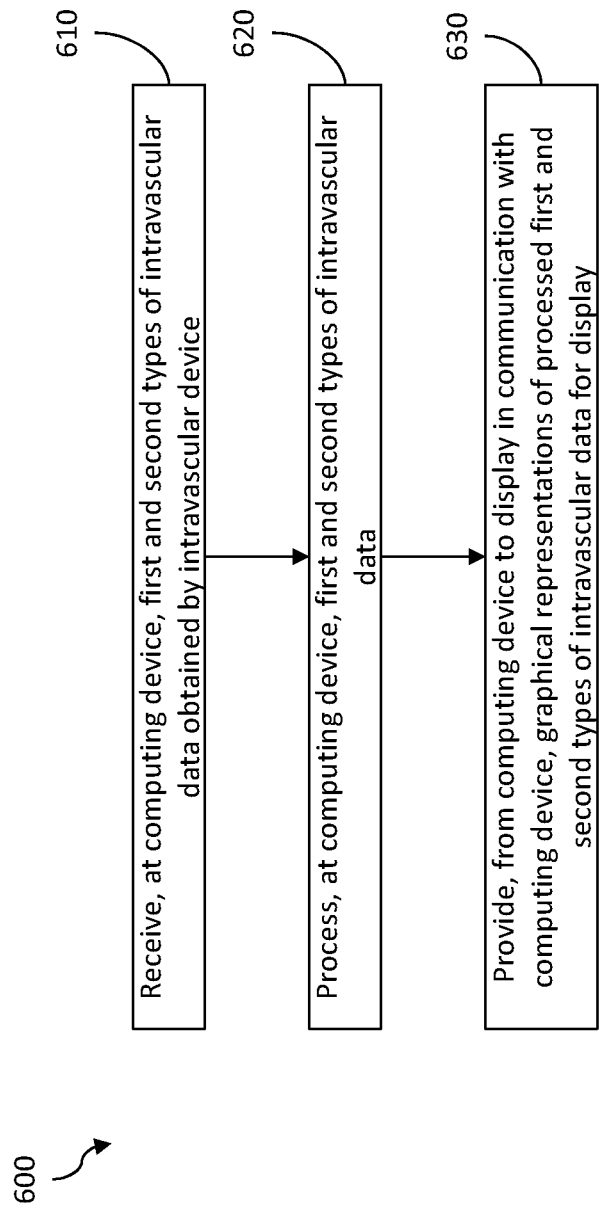
FIG. 6 is a flow diagram of a method of obtaining intravascular data according to aspects of the present disclosure.

FIG. 6 illustrates a flowchart of a method 600 of obtaining intravascular data. As illustrated, the method 600 includes a number of enumerated steps, but implementations of the method 600 may include additional steps before, after, and in between the enumerated steps. In some implementations, one or more of the enumerated steps may be omitted or performed in a different order. The steps of the method 600 may be performed by processor, such as the computing device 120 (FIG. 1).

At step 610, the method 600 includes receiving, at a computing device, first and second intravascular data associated with different modalities. The first and second intravascular data is obtained by an intravascular device inserted into the vasculature of a patient. The intravascular device is in communication with the computing device. The intravascular device may similar to the intravascular device 110 (FIGS. 1 and 2), including a flexible elongate member having a proximal portion and a distal portion, and a sensor assembly disposed at the distal portion of the flexible elongate member. The sensor assembly can include an array of CMUTs. The sensor assembly comprises or is operable to perform the functions of at least two of a pressure sensor, a flow sensor, or an imaging sensor.

In some embodiments, the first and second intravascular data are simultaneously obtained by the intravascular device. For example, different portions of the array of CMUTs can comprise or operate as different ones of the pressure sensor, the flow sensor, or the imaging sensor. In that regard, the method 600 can include controlling the respective different portions of the array of CMUTs to obtain pressure data, flow data, or imaging data.

In some embodiments, the first and second intravascular data are obtained by the intravascular device at different times. For example, the sensor assembly can comprise or operate as different ones of the pressure sensor, the flow sensor, or the imaging sensor at different times. In that regard, the method 600 can include controlling the sensor assembly to obtain pressure data, flow data, or imaging data at the respective different times.

At step 620, the method 600 includes processing, at the computing device, the first and second intravascular data. Processing the first and second intravascular data can include or more computational steps to filter, analyze, and/or otherwise manipulate the obtained data. In that regard, processing the first and second intravascular data can include determining an intravascular modality associated with the first and second intravascular data.

At step 630, the method 600 includes providing, from the computing device to a display in communication with the computing device, graphical representations of the processed first and second types of intravascular data for display. The graphical representations can include images of the patient's vasculature, quantities, colors, shading, and/or other suitable information representative of the processed data.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular device, comprising:
   a flexible elongate member having a proximal portion and a distal portion; and
   a first array of capacitive micromachined ultrasonic transducers (CMUTs) disposed at the distal portion of the flexible elongate member,
   wherein the first array of CMUTs is configured to obtain diagnostic data only such that the first array of CMUTs is not used for treatment,
   wherein the first array of CMUTs is operable as at least two different sensor types selected from the group consisting of a pressure sensor, a flow sensor, and an imaging sensor such that:
     at a first time, an individual CMUT of the first array of CMUTs obtains the diagnostic data corresponding to a first intravascular data type; and
     at a different, second time, the same individual CMUT obtains the diagnostic data corresponding to a different, second intravascular data type,
   wherein the first intravascular data type comprises a modality selected from the group consisting of intravascular pressure measurement, intravascular flow measurement, and intravascular imaging,
   wherein the different, second intravascular data type comprises a modality different from the first intravascular type,
   wherein the different modality is selected from the group consisting of the intravascular pressure measurement, the intravascular flow measurement, and the intravascular imaging, and
   wherein the intravascular pressure measurement and the intravascular flow measurement are different than the intravascular imaging such that the intravascular pressure measurement and the intravascular flow measurement do not obtain an image.

2. The intravascular device of claim 1, wherein the first array of CMUTs is disposed in an annular configuration around the flexible elongate member.

3. The intravascular device of claim 1, wherein the first array of CMUTs is disposed in at least one of a side-looking or forward-looking orientation.

4. The intravascular device of claim 1, further comprising: a second array of CMUTs.

5. The intravascular device of claim 4, wherein the first array of CMUTs is disposed in one of a side-looking or a forward-looking orientation, and wherein the second array of CMUTs is disposed in the other of the side-looking or the forward-looking orientation.

6. The intravascular device of claim 1, wherein the flexible elongate member comprises a guide wire or a catheter.

7. The intravascular device of claim 1, wherein the first array of CMUTs is arranged in a planar or non-planar configuration.

8. The intravascular device of claim 1, wherein different portions of the first array of CMUTs are operable as the at least two different sensor types.

9. An intravascular system, comprising:
   the intravascular device according to claim 1,
   a computing device in communication with the intravascular device and configured to receive the diagnostic data corresponding to the first and second intravascular data types obtained by the individual CMUT of the first array of CMUTs,
   wherein the computing device is configured to control the individual CMUT of the first array of CMUTs to:
     at the first time, obtain the diagnostic data corresponding to the first intravascular data type; and
     at the different, second time, obtain the diagnostic data corresponding to the different, second intravascular data type.

10. The intravascular system of claim 9,
    wherein different portions of the first array of CMUTs are operable as the at least two different sensor types, and
    wherein the computing device is configured to control the different portions of the first array of CMUTs to obtain, respectively, the diagnostic data corresponding to the first intravascular data type and the diagnostic data corresponding to the different, second intravascular data type.

11. The intravascular system of claim 9, wherein the first array of CMUTs is operable as the at least two different sensor types at the first time and the different, second time, and
wherein the computing device is configured to control the first array of CMUTs to:
at the first time, obtain the diagnostic data corresponding to the first intravascular data type; and
at the different, second time, obtain the diagnostic data corresponding to the different, second intravascular data type.

12. A method of obtaining intravascular data, the method comprising:
controlling, using a computing device, an array of CMUTs positioned at a distal portion of an intravascular device inserted into vasculature of a patient to obtain diagnostic data only such that the array of CMUTs is not used for treatment, wherein the controlling comprises:
controlling an individual capacitive micromachined ultrasonic transducer (CMUT) of the array of CMUTs to obtain, at a first time, the diagnostic data corresponding to a first intravascular data type; and
controlling the same individual CMUT to obtain, at a different, second time, the diagnostic data corresponding to a different, second intravascular data type, wherein the first intravascular data type comprises a modality selected from the group consisting of intravascular pressure measurement, intravascular flow measurement, and intravascular imaging, and wherein the different, second intravascular data type comprises a modality different from the first intravascular type, wherein the different modality is selected from the group consisting of the intravascular pressure measurement, the intravascular flow measurement, and the intravascular imaging;
processing, at the computing device, at least the diagnostic data corresponding to the first intravascular data type and the diagnostic data corresponding to the second intravascular data type; and
providing, from the computing device to a display in communication with the computing device, graphical representations of at least the processed diagnostic data corresponding to the first intravascular data type and the processed diagnostic data corresponding to the second intravascular data type for display,
wherein the array of CMUTs is operable as at least two different sensor types selected from the group consisting of a pressure sensor, a flow sensor, and an imaging sensor, and
wherein the intravascular pressure measurement and the intravascular flow measurement are different than the intravascular imaging such that the intravascular pressure measurement and the intravascular flow measurement do not obtain an image.

13. The method of claim 12,
wherein different portions of the array of CMUTs are operable as the at least two different sensor types,
wherein the method further comprises controlling the respective different portions of the array of CMUTs to obtain, respectively, the diagnostic data corresponding to the first intravascular data type and the diagnostic data corresponding to the different, second intravascular data type.

14. The method of claim 12,
wherein the array of CMUTs is operable as the at least two different sensor types at the first time and the different, second time, and
wherein the method further comprises controlling the array of CMUTs to:
at the first time, obtain the diagnostic data corresponding to the first intravascular data type; and
at the different, second time, obtain the diagnostic data corresponding to the different, second intravascular data type.

15. The method of claim 12, wherein the intravascular device comprises a flexible elongate member having a proximal portion and a distal portion, wherein array of CMUTs is disposed at the distal portion of the flexible elongate member.

16. The intravascular device of claim 1,
wherein the first intravascular data type comprises the intravascular imaging, and
wherein the second intravascular data type comprises the intravascular pressure measurement or the intravascular flow measurement.

* * * * *